United States Patent [19]

Gobetti et al.

[11] Patent Number: 4,563,443
[45] Date of Patent: Jan. 7, 1986

[54] ACETYLSALICYLIC ACID THIOESTERS, A PROCESS FOR THEIR PREPARATION AND PHARMACEUTICAL COMPOSITIONS CONTAINING THEM

[75] Inventors: Marino Gobetti, Milan; Guido Vandoni, Correzzana, both of Italy

[73] Assignee: Edmond Pharma S.r.l., Italy

[21] Appl. No.: 521,715

[22] Filed: Aug. 9, 1983

[30] Foreign Application Priority Data

Sep. 7, 1982 [IT] Italy ................................. 23141 A/82

[51] Int. Cl.$^4$ .................... A61K 31/265; A61K 31/71; C07C 153/023; C07J 15/00
[52] U.S. Cl. ................................. 514/29; 260/455 R; 514/513; 536/7.4
[58] Field of Search ................ 260/455 R; 424/301; 514/513; 536/7.4; 514/29

[56] References Cited

U.S. PATENT DOCUMENTS 4,256,761 3/1981 Suh et al. ................ 260/455 R

OTHER PUBLICATIONS

Noller, Textbook of Organic Chemistry, 3rd Ed., W. B. Saunders Co., Philadelphia, 1966, p. 261.

*Primary Examiner*—Henry R. Jiles
*Assistant Examiner*—Robert C. Whittenbaugh
*Attorney, Agent, or Firm*—Ostrolenk, Faber, Gerb & Soffen

[57] ABSTRACT

Acetylsalicylic acid thioesters having antipyretic activity and useful for the symptomatic treatment of influenza of formula:

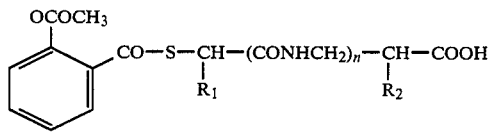

wherein n is zero or 1, $R_1$ is hydrogen, methyl or carboxy and $R_2$ is hydrogen or an acetamido group; a process for their preparation by reacting a functional derivative of acetylsalicylic acid with the suitable thiol; and pharmaceutical compositions containing them as active ingredient.

18 Claims, No Drawings

ACETYLSALICYLIC ACID THIOESTERS, A PROCESS FOR THEIR PREPARATION AND PHARMACEUTICAL COMPOSITIONS CONTAINING THEM

The present invention relates to novel acetylsalicylic acid thioesters having antipyretic activity and useful in the symptomatic treatment of influenza.

More particularly, the present invention provides novel acetylsalicylic acid thioesters of formula:

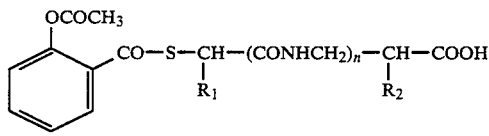

wherein n is zero or 1, $R_1$ is hydrogen, methyl or carboxy and $R_2$ is hydrogen or an acetamido group.

Particularly preferred are the compounds of formula I above, wherein when n is 1, $R_1$ is methyl and $R_2$ hydrogen and wherein when n is zero, $R_1$ is hydrogen and $R_2$ is acetamido or $R_1$ is carboxy and $R_2$ hydrogen.

The present invention further provides a process for the preparation of the compounds of formula I above, which comprises reacting a functional derivative of acetylsalicylic acid with a thiol of formula:

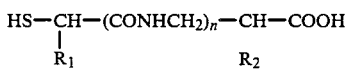

wherein n, $R_1$ et $R_2$ are as defined above, in an organic solvent at a temperature of from $-10°$ C. to $+50°$ C.

The anhydride, a mixed anhydride or an active ester can be advantageously employed as a suitable functional derivative of acetylsalicylic acid.

Particularly preferred functional derivatives are the acetylsalicylic acid anhydride and the acetylsalicylic acid/monoethyl carbonate mixed anhydride.

The functional derivatives of the acetylsalicylic acid are known; according to a preferred embodiment, they are prepared and reacted in situ with the compounds of formula II. As the organic solvent, ethyl acetate is advantageously used, but other solvents, such as acetone, methylene chloride or an hydrocarbon like hexane and toluene can be employed.

The reaction can be carried out in the presence of a tertiary organic base such as triethylamine.

The final product is isolated according to the usual methods, by eliminating the impurities, the unreacted starting materials inclusive, by evaporating the solvent and crystallizing.

The product thus obtained can be transformed into one of its pharmaceutically acceptable salts by treatment with a salifying agent such as an alkaline or an alkaline-earth hydroxide or with an organic, optionally amphoteric base.

Exemplary bases which can salify the acids of formula I above are the sodium, calcium and zinc hydroxides among the inorganic bases, and lysine, arginine, erythromycine, propionylerythromycine, dimethylaminoethanol and analogs among the organic bases or amphoteric compounds.

The novel thioesters of the present invention possess particularly interesting pharmacological properties. In particular the compounds of formula I and their salts have an antipyretic and mucolytic activity and are particularly useful as active ingredients in pharmaceutical compositions useful for the symptomatic treatment of influenza, in which the respiratory tract is involved.

Thus, the present invention provides pharmaceutical compositions containing, as active ingredient, a compound of formula I above or a pharmaceutically acceptable salt thereof (as above defined).

In the pharmaceutical compositions of the present invention for the oral, intramuscular or rectal administration, the compound of formula I can be administered in dosage unit form in admixture with the common pharmaceutical carriers and vehicles, to animals and humans for the treatment of febrile states in which the upper respiratory tract is involved and in general for the symptomatic treatment of influenza.

Salts of the compounds of formula I with antibiotics, such as erythromycine, erithromicinemonopropionate, hereinafter designated "propionylerythromicine", or other macrolides are particularly suitable for the treatment of febrile states due to bacterial infections of the upper respiratory tract.

The pharmaceutical compositions in dosage unit form include the forms for oral administration such as tablets, capsules, sachets containing powders or granules, as well as oral solutions or suspensions, vials for parenteral administration and suppositories for rectal administration.

Each unit dose can comprise from 100 to 2000 mg of active ingredient in admixture with the pharmaceutical carrier. Such an unit dose can be administered once to four times daily. The following examples illustrate the invention without limiting it.

EXAMPLE 1

To a mixture of 180 g of acetylsalicylic acid, 700 ml of ethyl acetate and 108 g of ethyl chloroformate, cooled at 0° C. under stirring, a mixture of 101 g of triethylamine and 300 ml of ethyl acetate, previously cooled at 0° C., is slowly added, by maintaining the temperature at 0°–10° C., then the mixture is allowed to reach 20° C., the precipitate is filtered off and washed with ethyl acetate.

To the solution of the acetylsalicylic acid/monoethyl carbonate mixed anhydride thus obtained 163 g of alpha-mercaptopropionylglycine are added, then the mixture is stirred 60 minutes, cooled at 10° C. and mixed with a solution of 101 g of triethylamine in 300 ml of ethyl acetate without allowing the temperature to exceed 20° C. The mixture is washed with 100 ml of hydrogen chloride at pH 3, and then with 100 ml of water. The organic phase is separated, dried over anhydrous sodium sulfate and concentrated under reduced pressure. An oil is obtained which crystallizes after two hours.

The solid thus obtained is taken up with water, filtered and dried. Thus, there are obtained 272 g of 2-(2-acetoxybenzoylthio)propionylglycine (formula I, n=1, $R_1=CH_3$, $R_2=H$) which is crystallized from ethyl acetate; m.p. 100°–102° C. 0.1 ml of 2-(2-acetoxybenzoyl-thio)propionylglycine and 0.1 ml of sodium bicarbonate are reacted in an equilibrium water/dioxane mixture at a temperature below 10° C. By lyophilization of the mixture, the sodium salt of 2-(2-acetoxybenzoylthio)-propionylglycine is obtained.

To a solution of 0.1 mol of 2-(2-acetoxybenzoylthio)-propionylglycine and 0.1 mol of erithromicine in ethyl acetate, 5 ml of water are added, then the precipitate thus obtained is filtered off and dried. Thus, the erithromycine salt of 2-(2-acetoxybenzoylthio)propionylglycine is obtained.

To a solution of 0.1 mol of 2-(2-acetoxybenzoylthio)propionylglycine in isopropanol, 0.2 mol of DL-lysine and then 5 ml of water are added. Thus there is obtained a homogeneous solution from which the DL-lysine salt of 2-(2-acetoxybenzoylthio)propionylglycine which crystallizes spontaneously, is filtered and dried.

EXAMPLE 2

To a solution of acetylsalicylic acid/monoethylcarbonate mixed anhydride, obtained from 30 g of acetylsalicylic acid and 18 g of ethyl chloroformate in 200 ml of ethyl acetate in the presence of 16.8 g of triethylamine in 50 ml of ethyl acetate, there are added 25 g of mercaptosuccinic acid, then the mixture is stirred for 60 minutes, and mixed with a solution of 16.8 g of triethylamine in 50 ml of ethyl acetate. The suspension is stirred and the temperature rises to 30° C. After 30 minutes, 16.8 g of triethylamine are added and stirring is continued for 60 minutes. The mixture is washed with 100 ml of hydrogen chloride at pH 3 and then with water. The organic phase is dried over anhydrous sodium sulfate and concentrated at reduced pressure to obtain 52 g of pale-yellow oil which crystallizes after 30 days. The crystalline product thus obtained is taken up with water, filtered off, dried and recrystallized from chloroform.

Thus, there is obtained the 2-(2-acetoxybenzoylthio)succinic acid (formula I, n=O, $R_1$=COOH, $R_2$=H); m.p. 110–113 C. By treating the product thus obtained with the stoichiometrical amount of sodium hydrogen carbonate, erythromycine and DL-lysine, respectively, as described in example 1, the sodium, erythromycine and DL-lysine salts of 2-(2-acetoxybenzoylthio)succinic acid are obtained.

EXAMPLE 3

To a solution of acetylsalicylic acid/monoethylcarbonate mixed anhydride in ethyl acetate, prepared as described in example 1, 163 g of acetylcisteine are added and the mixture thus obtained is stirred 60 minutes at room temperature.

The mixture is cooled to 10° C. and a solution of 101 g of triethylamine in 300 ml of ethylacetate is added thereto at a temperature not higher than 20° C.

After a further 60 minutes stirring, the organic solution is washed with 100 ml of hydrogen chloride at pH 3, then with 1000 ml of water. The organic phase is dried over anhydrous sodium sulfate and concentrated under reduced pressure to obtain a yellow oil which crystallizes after 2 hours. The crystalline product is taken up with water, filtered off and dried to yield 242 g of 2-acetamido-3-(2-acetoxybenzoylthio)propionic acid (formula I, n=O, $R_1$=H, $R_2$=NHCOCH$_3$) which is crystallized from ethyl acetate; m.p. 120°–122° C. By operating as described in Example 1, the sodium, erythromycine and DL-lysine salts of 2-acetamido-3-(2-acetoxybenzoylthio)propionic acid are prepared.

EXAMPLE 4

To a solution of 0.1 mol of propionylerythromycine and 0.1 ml of 2-(2-acetoxybenzoylthio)propionylglycine in 50 ml of cyclohexane, 5 ml of methanol are added under stirring. After a 60 minutes stirring, the precipitate is filtered off and dried. Thus, there is obtained the propionylerythromycine salt of 2-(2-acetoxybenzoylthio)propionylglycine.

In the same manner, the propionylerythromycine salt of 2-acetamido-3-(2-acetoxybenzoylthio)propionic acid is prepared.

EXAMPLE 5

Capsules are prepared having the following compositions

| | |
|---|---|
| 2-(2-acetoxybenzoylthio)propionylglycine | 300 mg |
| corn starch | 400 mg |

In the same manner, capsules containing 300 mg of the propionylerythromycine salt of 2-(2-acetoxybenzoylthio)propionylglycine or 300 mg of the erythromycine salt of 2-(2-acetoxybenzoylthio)propionylglycine are prepared.

EXAMPLE 6

Granules for the reconstitution into a liquid oral formulation having the composition set forth herein below are prepared.

| | |
|---|---|
| DL-lysine salt of 2-(2-acetoxybenzoylthio)propionylglycine | 400 mg |
| saccharose | 5000 mg |
| citric acid | 10 mg |
| trisodium citrate | 90 mg |
| sodium 4-hydroxybenzoate | 25 mg |
| saccharin | 15 mg |
| flavoring agent (orange) | 50 mg |

The granulate, prepared according the conventional techniques, is introduced in sachets each containing 400 mg of active ingredient.

We claim:

1. A thioester of acetylsalicylic acid of formula

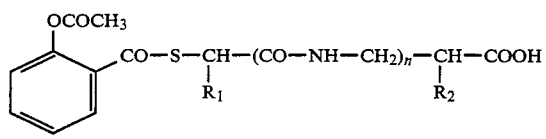

wherein $R_1$ is hydrogen, methyl or carboxy, $R_2$ is hydrogen or acetamido and n is zero or 1 or a pharmaceutically acceptable salt thereof.

2. A thioester of acetylsalicylic acid as claimed in claim 1 which is the 2-(2-acetoxybenzoylthio)succinic acid or pharmaceutically acceptable salt thereof.

3. A thioester of acetylsalicylic acid as claimed in claim 1 which is the 2-acetamido-3-(2-acetoxybenzoylthio)propionic acid or pharmaceutically acceptable salt thereof.

4. The 2-(2-acetoxybenzoylthio)propionylglycine or a pharmaceutically acceptable salt thereof.

5. A pharmaceutical composition having antipyretic and mucolytic activity comprising, as active ingredient an antipyretic effective amount of a thioester of acetylsalicylic acid as claimed in claim 1 together with suitable carrier and/or excipient.

6. A composition as claimed in claim 5 which is in dosage unit form.

7. A composition as claimed in claim 6 comprising from 100 to 2000 mg of active ingredient per dosage unit in admixture with a pharmaceutical carrier.

8. A thioester of acetylsalicylic acid as claimed in claim 2 in which the salt is the sodium, erythromycine, or DL-lysine salt thereof.

9. A thioester of acetylsalicylic acid as claimed in claim 3 in which the salt is the sodium, erthromycine, or DL-lysine salt thereof.

10. A thioester of acetylsalicylic acid as claimed in claim 4 in which the salt is the sodium, erythromycine, or DL-lysine salt thereof.

11. A composition as claimed in claim 5 in which n is 1, $R_1$ is methyl and $R_2$ is hydrogen.

12. A composition as claimed in claim 11 in which the salt is the sodium, erythromycine, or DL-lysine salt thereof.

13. A composition as claimed in claim 5 in which n is 0, $R_1$ is hydrogen, and $R_2$ is acetamido.

14. A composition as claimed in claim 13 in which the salt is the sodium, erythromycine, or DL-lysine salt thereof.

15. A composition as claimed in claim 5 in which n is 0, $R_1$ is carboxy and $R_2$ is hydrogen.

16. A composition as claimed in claim 15 in which the salt is the sodium, erythromycine, or DL-lysine salt thereof.

17. A composition as claimed in claim 7 in which the thioester is 2-(2-acetoxybenzoylthio)succinic acid, 2-acetamido-3-(2-acetoxybenzoylthio)propionic acid, 2-(2-acetoxybenzoylthio)propionylglycine or a pharmaceutically acceptable salt thereof.

18. A composition as claimed in claim 17 in which the salt is the sodium, erythromycine, or DL-lysine salt thereof.

* * * * *